(12) United States Patent
Goelen et al.

(10) Patent No.: US 8,333,124 B2
(45) Date of Patent: Dec. 18, 2012

(54) DIFFUSIVE SAMPLING DEVICE

(75) Inventors: Eddy Goelen, Geel (BE); Robert Bormans, Koersel (BE)

(73) Assignee: Vlaamse Instelling Voor Technologisch Onderzoek (Vito), Mol (BE)

( * ) Notice: Subject to any disclaimer, the term of this patent is extended or adjusted under 35 U.S.C. 154(b) by 1195 days.

(21) Appl. No.: 11/667,441

(22) PCT Filed: Nov. 7, 2005

(86) PCT No.: PCT/BE2005/000155
§ 371 (c)(1),
(2), (4) Date: Oct. 19, 2007

(87) PCT Pub. No.: WO2006/047839
PCT Pub. Date: May 11, 2006

(65) Prior Publication Data
US 2011/0142733 A1 Jun. 16, 2011

(30) Foreign Application Priority Data

Nov. 8, 2004 (EP) ..................................... 04447244

(51) Int. Cl.
*G01N 1/22* (2006.01)
(52) U.S. Cl. .......................................................... 73/864
(58) Field of Classification Search ............... 73/866, 73/31.02, 31.03, 31.05, 863–864; 422/61
See application file for complete search history.

(56) References Cited

U.S. PATENT DOCUMENTS 3,985,017 A * 10/1976 Goldsmith .................... 436/116
4,158,958 A    6/1979 Braun

FOREIGN PATENT DOCUMENTS

| EP | 1 059 520 A2 | 12/2000 |
| FR | 2 621 691 | 4/1989 |
| GB | 2 078 371 A | 1/1982 |

OTHER PUBLICATIONS

Plastics Design Library Staff (1997). Handbook of Plastics Joining. (pp. 130). William Andrew Publishing/Plastics Design Library.*

* cited by examiner

*Primary Examiner* — Peter Macchiarolo
*Assistant Examiner* — Jamar Ray
(74) *Attorney, Agent, or Firm* — Merchant & Gould P.C.

(57) ABSTRACT

A kit of parts is for assembling a diffusive dosimeter for the detection of pollutants, said kit of parts includes a housing (1, 50), a first adsorbant (2) to be placed inside the housing and a first spacer (3) to be placed on top of the adsorbant, to define a thickness (L) and a first surface area (A) of a diffusive layer. The kit also has a first protective layer (5) placed on top of the spacer and a first cover (6) having an opening (7), to be placed on top of the protective layer, in a manner to close off the assembled dosimeter at its circumference. The kit has at least one or more additional spacers (15,16,17), each additional spacer being able to replace the first spacer and each spacer defines a different surface area, so that each spacer allows a measurement with a different uptake rate.

14 Claims, 7 Drawing Sheets

DIFFUSIVE SAMPLING DEVICE

FIELD OF THE INVENTION

The present invention is related to a diffusive sampling device or 'dosimeter' used for the detection of pollutants in a gaseous fluid, primarily in air, and for the measurement of the concentration of such pollutants.

STATE OF THE ART

Diffusive sampling devices of this kind have been described in the art. They comprise an adsorbant which is able to react with or adsorb a particular pollutant, when exposed to a gas mixture, e.g. ambient air of an indoor workplace. The pollutant is able to diffuse towards said adsorbant through a diffusive portion, which may be an air gap or a portion of porous material, or a combination of both. From the uptake of pollutant by the adsorbant, the concentration of the pollutant in the air may then be calculated, based on the knowledge of the diffusive portion's dimensions and the pollutant's diffusion coefficient in said diffusive portion.

Known diffusive dosimeters are described in U.S. Pat. No. 4,158,958, GB-A-2078371 and FR-A-2621691. A problem with existing dosimeters is that they are produced as a kind of 'black box'. They have fixed dimensions leading to a fixed uptake rate for each pollutant, i.e. the mass of pollutant adsorbed per unit of time.
As the time of a measurement is often fixed, e.g. 8 h for a workplace test, it is a problem that the uptake rate cannot be adapted to the test conditions by the user of the device. Ambient air with low pollutant concentrations may require a higher uptake rate, and vice versa. When a fixed high uptake rate is applied, there is a danger of oversaturation of the adsorbant, while a low uptake rate may cause the adsorbed pollutant to remain below the detection limit.

AIMS OF THE INVENTION

The present invention aims to provide a modular diffusive dosimeter which allows a higher degree of flexibility in its operation. The flexibility is a choice of uptake rate and thus mass adsorbed with one and the same sampler without changing external sampler geometry, sampling time and exposure concentration.

SUMMARY OF THE INVENTION

The invention is related to a modular diffusive dosimeter with variable uptake rate as described in the appended claims.

SHORT DESCRIPTION OF THE DRAWINGS

Figure 1:
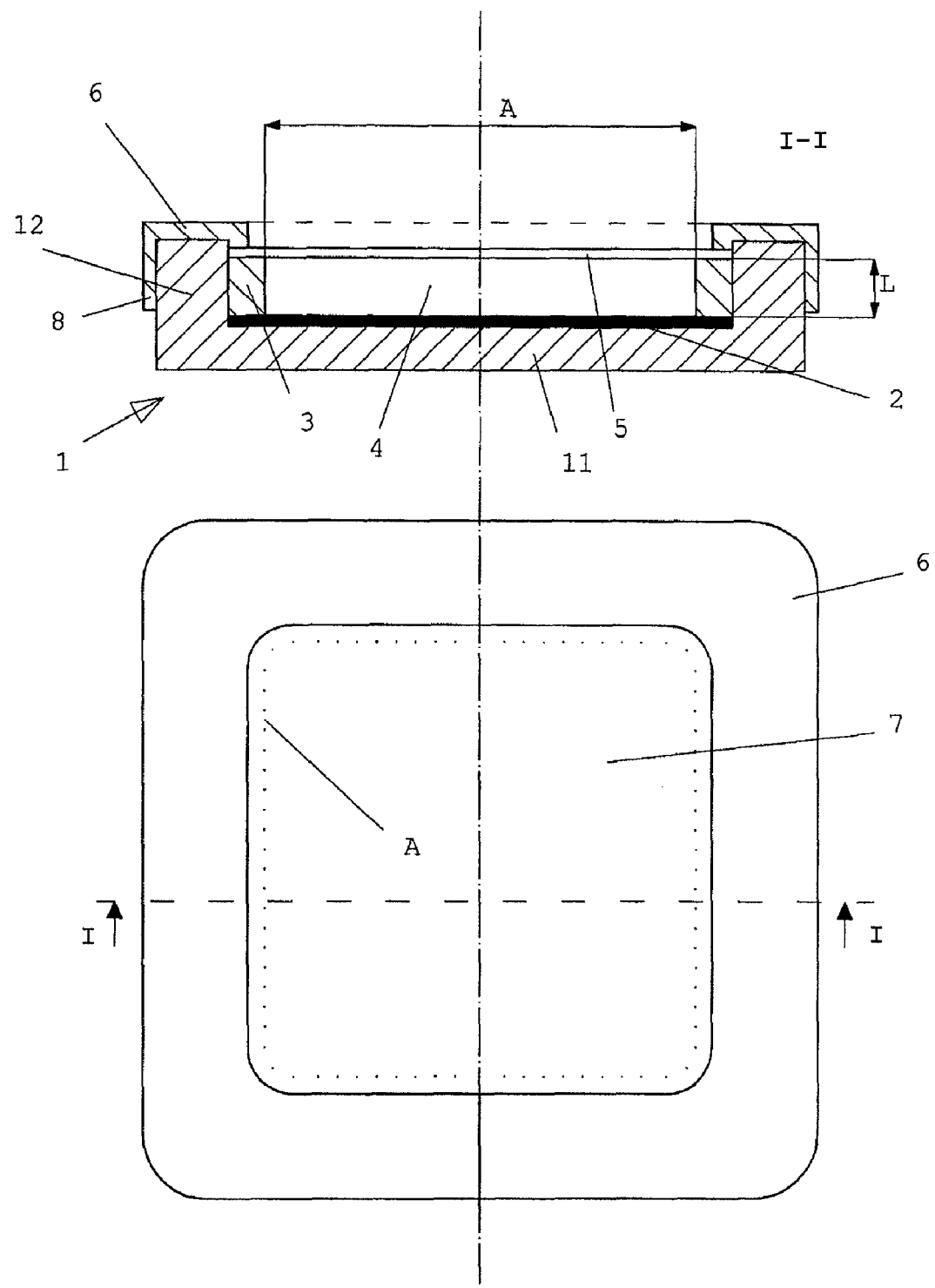
Figure 2:
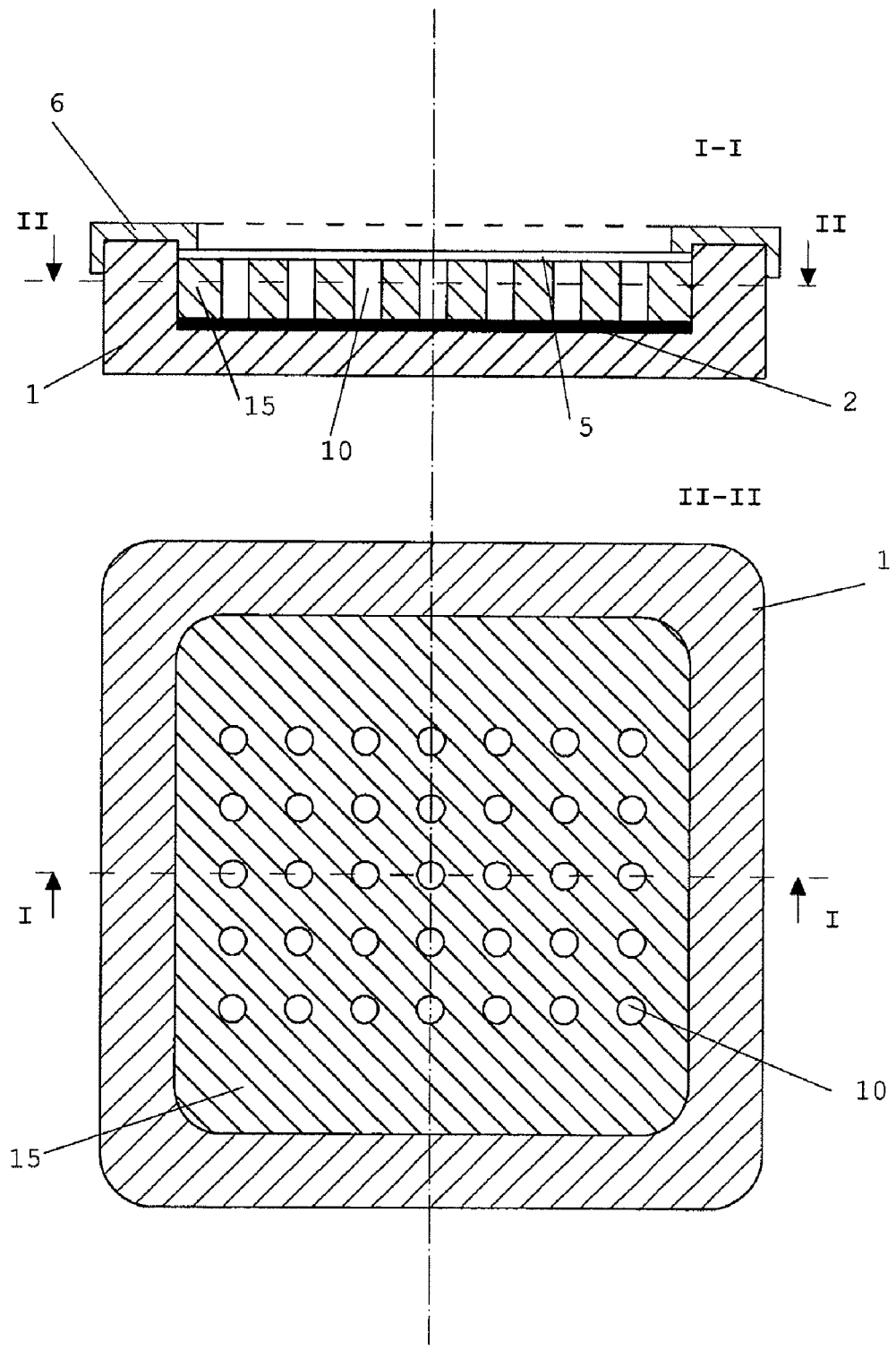
Figure 3:
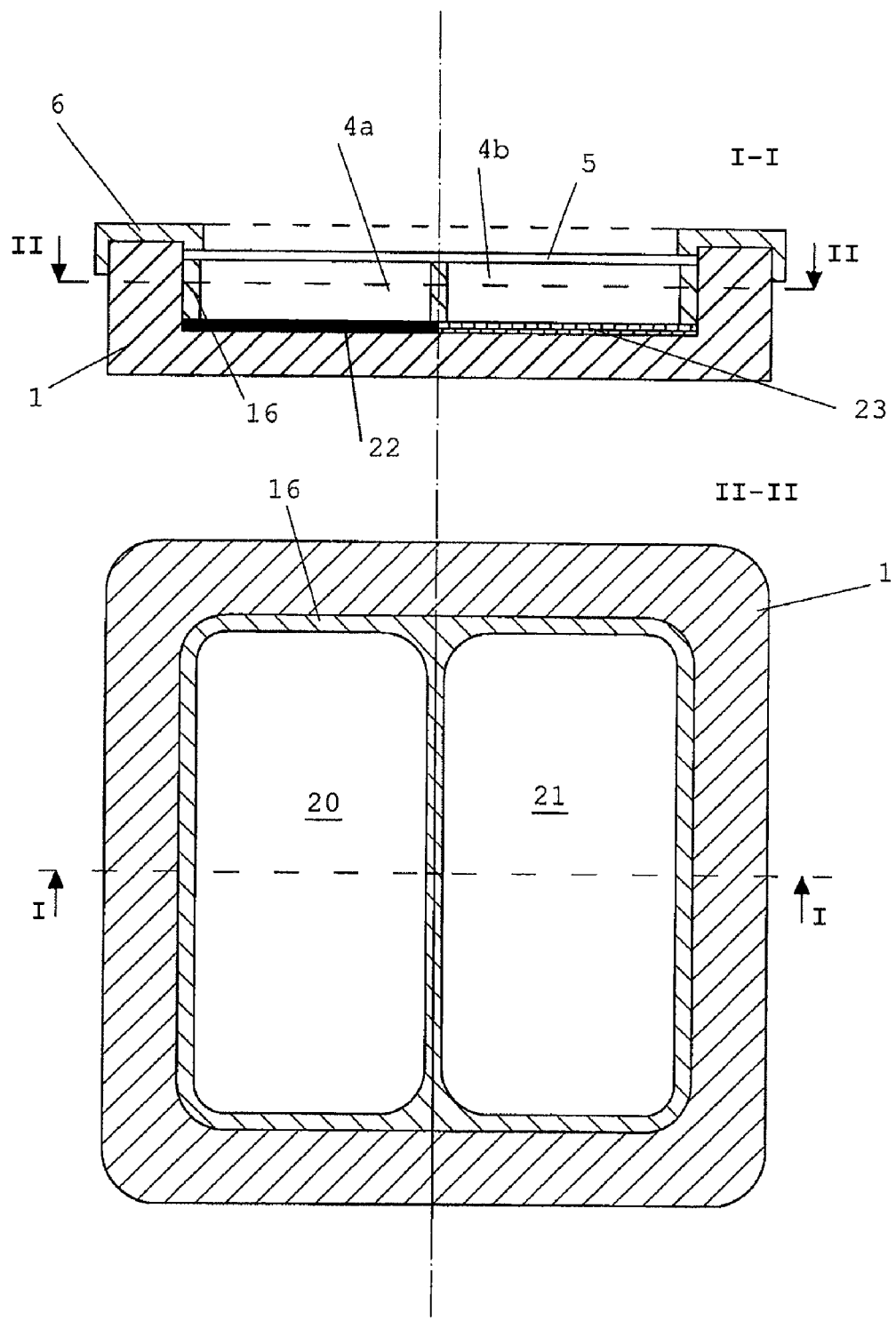
Figure 4:
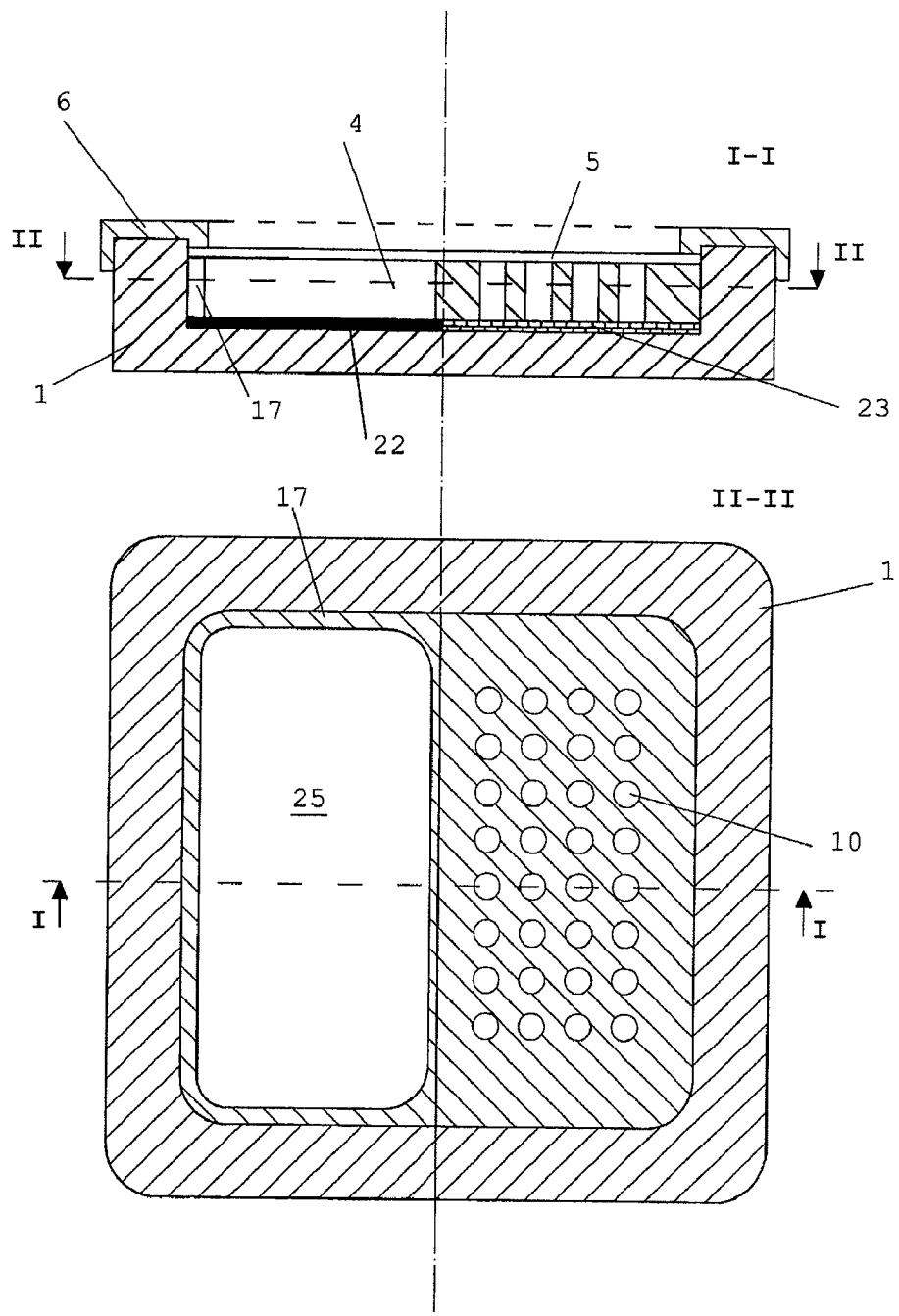

FIG. 1 represents a dosimeter of the invention, having an open cover and a first spacer element.
FIG. 2 represents the same dosimeter, wherein a spacer is provided comprising small holes.
FIG. 3 represents the same dosimeter, wherein a spacer is provided which allows the application of two different adsorbents.
FIG. 4 represents the same dosimeter, wherein a spacer is provided with two halves, each halve having a different uptake rate.
FIGS. 5a, 5b, 6a, 6b, and 7 show prototypes of a dosimeter according to the invention.

DETAILED DESCRIPTION OF THE INVENTION

Based on Fick's diffusion law, the concentration of a pollutant in a gas mixture, said pollutant having diffused through a diffusive layer, can be expressed as:

$$C_0 = \frac{m \cdot L}{D \cdot A \cdot t}$$

wherein m is the uptake of pollutant (in mg), L is the length of the diffusion path (cm), D is the diffusion coefficient of the pollutant in the diffusive layer (cm$^2$/s), A is the surface of the diffusive layer (cm$^2$), and t is the uptake time (sec).
When defining the uptake rate Q as D·A/L, this becomes:

$$C_0 = \frac{m}{Q \cdot t}$$

As mentioned above, in existing dosimeters, Q is a constant value for a particular pollutant type. The adsorbed amount (m) can only be changed by changing the sampling time (t) or when $C_o$ changes. In the dosimeter of the invention, means are provided for the user to adapt the uptake rate as a function of the ambient conditions, without changing the external dimensions of the device. The basic idea is to provide a modular dosimeter, wherein one or more sub-parts can be exchanged by the user so that the use of a particular part results in a particular value of the parameters A and L, thereby leading to a variable uptake rate Q.

FIG. 1 shows a schematic view of a dosimeter according to the invention. It comprises a housing 1, which may be a square shaped receptacle formed by a bottom plate 11 and a vertical circumferential wall 12 as shown in the drawing. On the bottom of the housing is the adsorbant 2, a layer of a suitable material, able to take up the pollutant by physical or chemical reactions. A spacer 3 is then present on top of the adsorbant. The spacer is essentially a ring-shaped part of the same form as the housing, and which has the function of creating an air gap 4 playing the part of the diffusive layer (still air zone). At the top of the spacer 3 is a protective layer 5, which is permeable by the pollutant but which stops convection currents from entering the dosimeter, so that the air in the air gap remains essentially undisturbed. The dosimeter is closed by a cover 6. The cover is easily removable from the device. The cover 6 shown in FIG. 1 has an opening 7. This results in a dosimeter with a given uptake factor Q, defined by the diffusion length L, and the surface A of the air gap region. Cover 6 can be replaced for transport by a closed cover. The cover of the preferred embodiment of the invention has a circumferential wall 8, which overlaps with the wall of the housing, thereby closing off the dosimeter at the sides. This aspect will be better described based on the prototype drawings in FIGS. 5 to 7.

According to the invention, the spacer 3 can be replaced by another spacer with a different surface area A. For example, the spacer 15 shown in FIG. 2 can be used, which has a number of cylindrical holes 10 through the thickness of the spacer. Installation of spacer 15 will have the effect of a reduction of the surface A and thus a change in uptake rate for a particular pollutant. By providing a set of spacers with varying amounts of holes through their thickness, said holes possibly having varying diameters, the user has the possibility to select the suitable spacer which will give rise—for a particular pollutant—to the optimum uptake rate.

FIG. 3 shows another type of spacer 16 which can be installed in stead of the previously described model 3. Spacer 16 has two large openings 20 and 21. This spacer part is suitable to be used in combination with two different adsorbant layers 22 and 23, corresponding to the two openings, each adsorbant being adapted to measure a different pollutant. Alternatively, spacer 16 of FIG. 3 can be used with an adsorbant 2 of one particular type, as shown in FIG. 1. In this way, the two halves of the adsorbant are taking up pollutant through separated air gaps 4a and 4b. After exposure, the adsorbant can then be cut in two parts, which can be analysed separately, possibly by applying different analytical procedures. It is equally possible to place two adsorbant layers of the same type, side by side, in combination with the spacer 16 of FIG. 3. The two adsorbants can then be analysed separately after the test. Spacers of type 16 can be provided having more than two openings.

One particular embodiment of a spacer has one large opening 25 on one half of the spacer surface, and a number of cylindrical holes 10 on the other half (see spacer 17 in FIG. 4). This spacer allows to do a measurement with a different uptake rate for each sub-part of the dosimeter's surface. This type of spacer adds another dimension to the dosimeter, as it allows to do one measurement with two different uptake rates, thereby allowing to measure quantitatively different pollutants using the same adsorbant, as well as the same pollutant over a very different concentration range. Of course, the spacer 17 can also be used with different adsorbants under each subpart, thereby allowing a further variation in the measurement conditions.

Apart from the spacer (3,15,16,17), also the adsorbant 2 and the protective layer 5 are easily removable from the device and can be replaced by adsorbants or protective layers chosen from a set of these items provided to the user, for example for adapting the dosimeter to another type of pollutant. For this purpose these layers are preferably self-supporting, i.e. sufficiently rigid so that they can be easily taken out of the device by the user. Finally, a set of covers 6 may be provided, with different sizes of aperture 7.

So in the first place, the invention is related to a 'kit-of-parts', comprising at least:
 a housing 1
 a first adsorbant 2
 a first spacer 3, to define the thickness L and a first surface area A of the diffusive layer,
 a first protective layer 5
 a first cover 6 having an opening 7
and further comprising at least one or more additional spacers, preferably having the same thickness L, each additional spacer being able to replace said first spacer, wherein each spacer defines a different surface area, so that each spacer allows to do a measurement with a different uptake rate. This leads to the concept of a multi-uptake rate sampler.

In particular, each spacer comprises openings through the thickness of the spacer, said openings having an essentially constant cross-section, said openings defining the surface area A. The openings in one spacer are different in number, size or shape from the openings in another spacer, so that different spacers allow to do a measurement with different uptake rates.

In other words, each spacer partitions the surface of the adsorbant in a different way, allowing to expose a different portion of the adsorbant to the pollutant, thereby leading to a variation of the parameter 'A' in the formula of Fick's law. For a given length 'L' of the diffusive path, and a particular diffusion layer (preferably air), this leads to a variation of the uptake rate Q (also within one and the same sampler, e.g. when the spacer of FIG. 4 is used).

Preferably, the set of spacers comprises one or more of the following: a spacer with a number of small holes, as shown in FIG. 2, a spacer with two large openings of the same size, as shown in FIG. 3, a spacer with one large opening on one half of the surface and small openings on the other, as shown in FIG. 4, the latter allowing a measurement with two different uptake rates within one and the same sampler.

Besides this, any spacer may be added which partitions the dosimeter's surface in another way, e.g. small holes on one quarter of the surface, small holes with another diameter on another quarter, and a large opening on the rest of the surface. Any combination of sizes and shapes or number of openings can be applied, as is clear to the skilled person.

According to the preferred embodiment, the kit of parts further comprises an additional closed cover, to replace the open cover 6 after the measurement, so that the dosimeter can be closed off and brought to the laboratory for analysis, without taking further precautions to make sure the adsorbant is no longer exposed to the atmosphere.

In stead of one adsorbant, the kit of parts of the invention may comprise different adsorbants, possibly in different sizes. For example, two different adsorbants may be provided, each corresponding to half the size of the housing's surface. These adsorbants can then be used in combination with a spacer as shown in FIG. 3 or 4. The kit of parts may equally comprise several additional protective layers, able to replace the first protective layer.

The kit of parts may further comprise a means for identifying the pre-defined uptake rate linked to a particular spacer, or to a part of a spacer (in the case of FIG. 4, e.g.). This means may be a list of values, identifying the spacers or sub-parts of the spacers in the kit of parts (e.g. by a number, appearing on the spacers themselves), and the corresponding uptake rates, preferably for a diffusion layer consisting of air, or possibly for different types of diffusion layers. Alternatively, the uptake rates may be printed on the spacers themselves.

The housing and cover of a dosimeter of the invention must be designed so that they can be easily separated and re-assembled, with a minimum of leakage between the housing and the cover through the sides of the device.

Figure 5B:
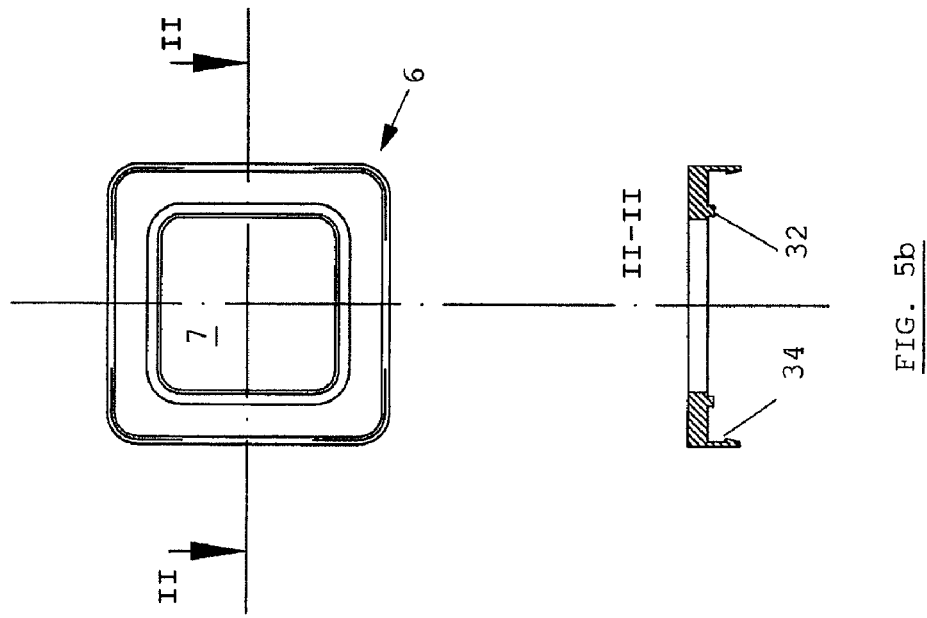
Figure 5A:
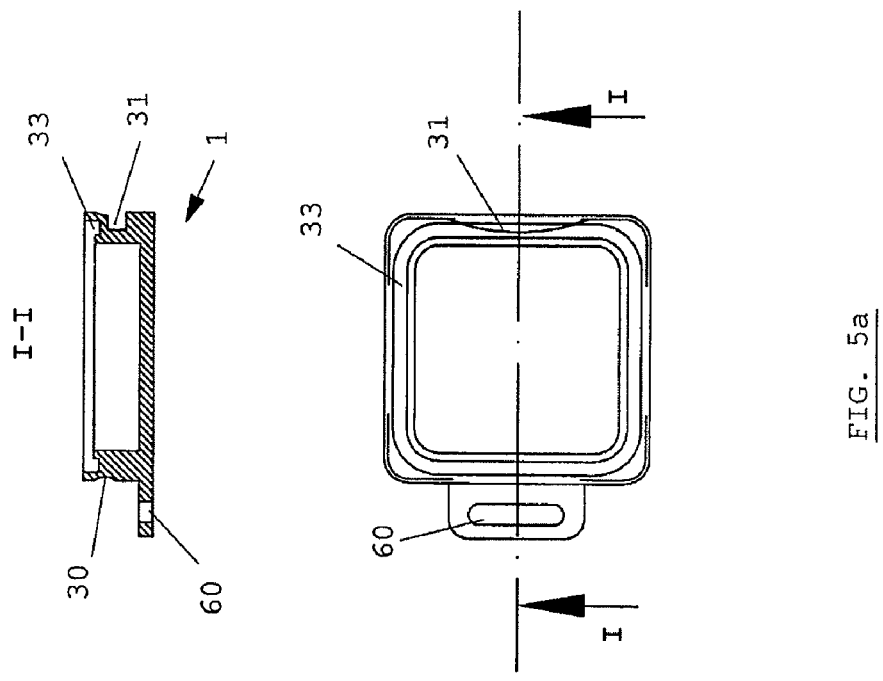

FIG. 5a shows a prototype of the dosimeter's housing according to the invention. A groove 30 is made in the outer wall of the housing. To one side of the housing, at position 31, the groove has a larger depth, in order to facilitate the removal of the cover. The cover 6 which is to be used with the housing of FIG. 5a is shown in FIG. 5b. It has a first protruding rim 32 arranged to be accommodated into a circumferential groove 33 at the top of the housing, for accurate positioning of the cover. On the vertical walls, the cover has a second protruding rim 34, arranged to fit into the groove 30 and thereby close off the housing at the sides.

Figure 6A:
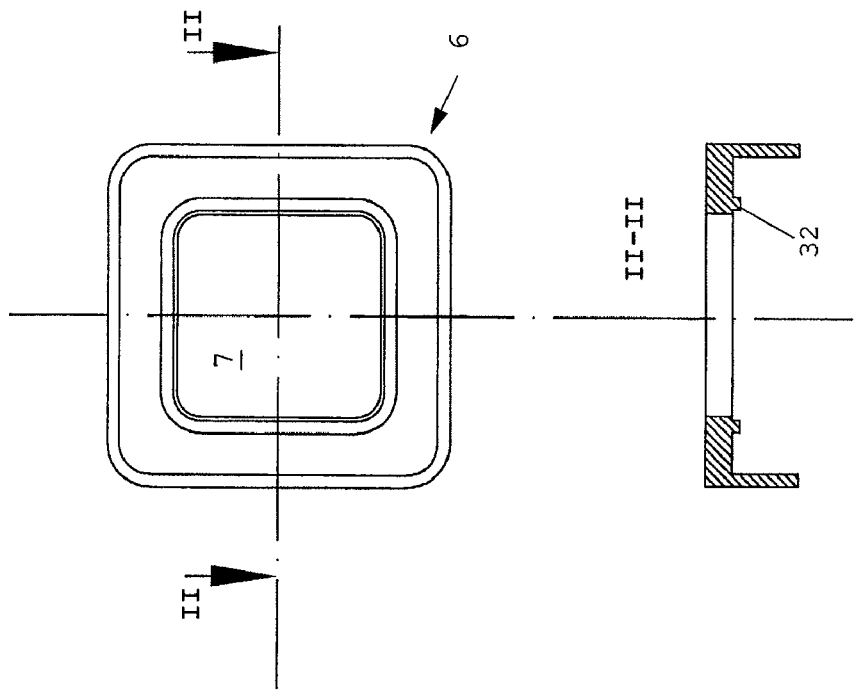
Figure 6B:
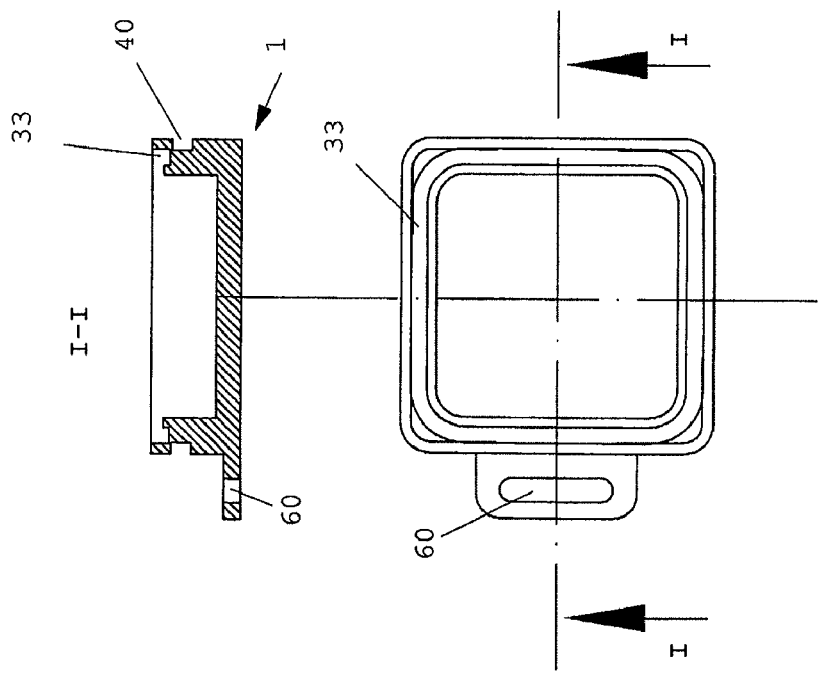

For improved closure of the housing at the sides, it is beneficial to apply an O-ring between the housing's outer wall 12 and the vertical wall 8 of the cover. For this purpose, the housing and cover shown in FIGS. 6a and 6b are suitable. This housing has a deep groove 40 around its circumference, into which the O-ring can be accommodated. The vertical wall 8 of the cover 6 does not have a protruding rim in this case.

Figure 7:
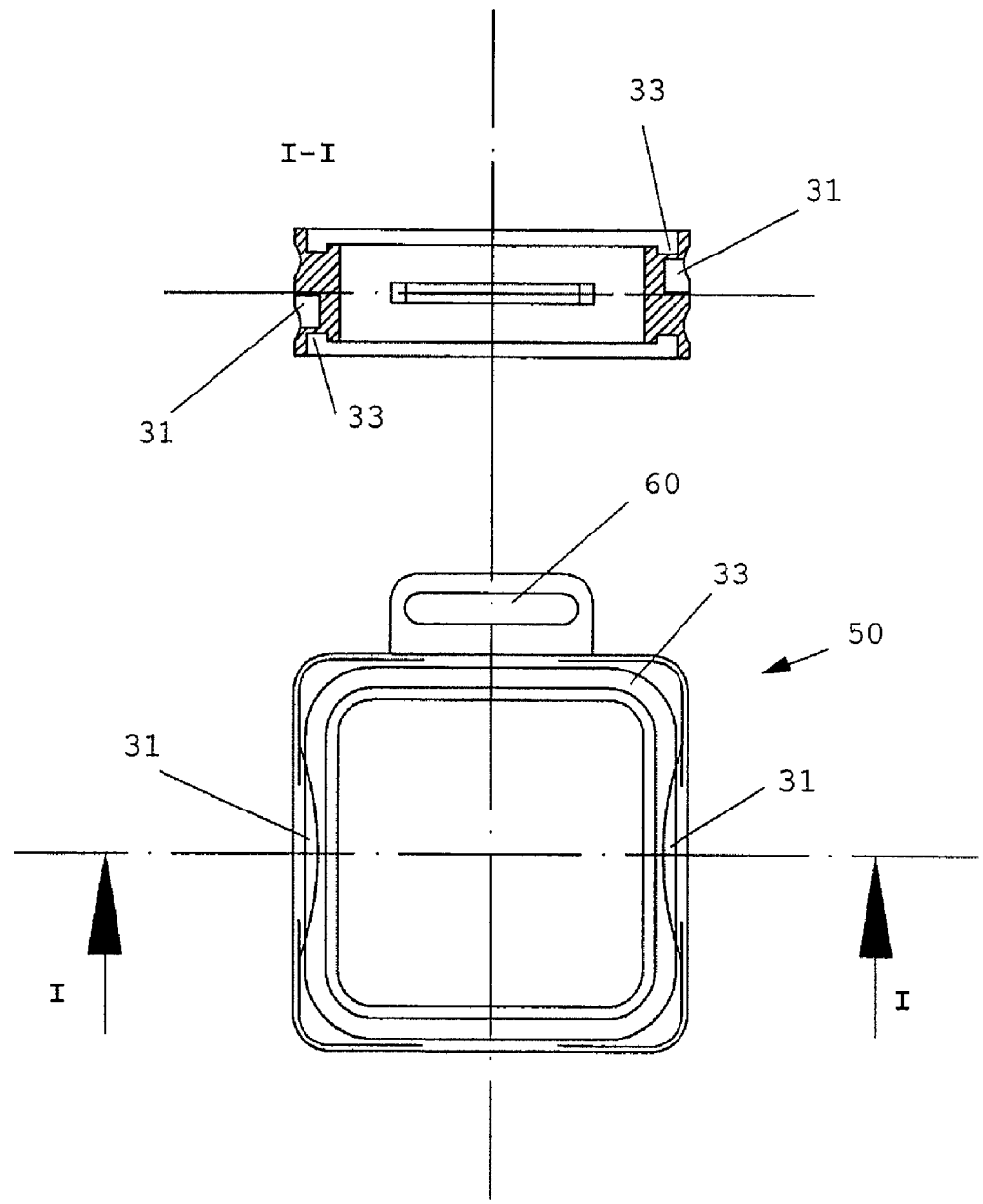

FIG. 7 shows another prototype with an open housing 50, to which a cover can be attached at both sides, so that the double amount of pollutant uptake is possible. All the embodiments of FIGS. 5, 6 and 7 are of the 'badge' type, i.e.

they can be attached to the wearer's clothes for example. To this aim, they have a connection ring 60 to one side of the housing.

The housing, cover and spacer parts can be made of PVC or an equivalent material. The protective layer 5 can be a layer of e.g. hydrophobic polyethylene with a thickness of 2 mm. The adsorbent can e.g. be a layer of carbon based material known in the art.

The invention claimed is:

1. A kit of parts for assembling a diffusive dosimeter for the detection of pollutants, said kit of parts comprising:
   a housing,
   a first adsorbent to be removably placed inside said housing,
   a first spacer to be removably placed on top of said adsorbent, to define a thickness and a first surface area of a diffusive layer,
   a first protective layer to be removably placed on top of said spacer,
   a first cover having an opening, to be removably placed on top of said protective layer, to close off the assembled dosimeter at the dosimeter's circumference,
   at least one additional spacer, each additional spacer being configured to replace said first spacer and defining the same thickness as the first spacer, wherein the first spacer and each additional spacer comprises one or more through-holes, the through-holes being different between the spacers so that each spacer defines a different surface area of the diffusive layer and provides for making a measurement with a different uptake rate, wherein the through-holes have a constant cross-section throughout the thickness;
   wherein at least one of said additional spacers comprises two through-holes of about equal size, wherein each of the two through-holes of about equal size extends substantially over about one-half of the spacer's surface.

2. The kit of parts according to claim 1, wherein at least one spacer defines a plurality of through-holes.

3. Kit of parts according to claim 1, further comprising one or more additional adsorbants.

4. Kit of parts according to claim 1, wherein said housing has a circumferential wall and said first cover has a circumferential wall, wherein in the assembled state, the wall of said first cover overlaps the wall of said housing to close off the dosimeter at the circumference.

5. Kit of parts according to claim 4, wherein said housing comprises a groove around the outer circumference of the circumferential wall.

6. Kit of parts according to claim 4, wherein said housing comprises a groove of constant depth along the outer circumference of the circumferential wall, said groove being adapted for receiving an O-ring.

7. Kit of parts according to claim 5, wherein said housing is rectangular shaped and said groove has a larger depth on one side of said housing configured to facilitate removal of the first cover.

8. Kit of parts according to claim 5, wherein said first cover comprises a protruding rim at the interior side of its circumferential wall.

9. Kit of parts according to claim 1, further comprising means for identifying a pre-defined uptake rate linked to one of said spacers.

10. The kit of parts according to claim 1, further comprising one or more additional protective layers.

11. The kid of parts according to claim 1, wherein the diameter is configured for accepting two distinct adsorbents, each of the adsorbents extending over a different through-hole.

12. A kit of parts for assembling a diffusive dosimeter for the detection of pollutants, said kit of parts comprising:
    a housing;
    a first adsorbent to be removably placed inside said housing;
    a first spacer to be removably placed on top of said adsorbent, to define a thickness and a first surface area of a diffusive layer;
    a first protective layer to be removably placed on top of said spacer;
    a first cover having an opening, to be removably placed on top of said protective layer, to close off the assembled dosimeter at the dosimeter's circumference;
    at least one additional spacer, each additional spacer being configured to replace said first spacer and defining the same thickness as the first spacer, wherein the first spacer and each additional spacer comprises one or more through-holes, the through-holes being different between the spacers so that each spacer defines a different surface area of the diffusive layer and provides for making a measurement with a different uptake rate, wherein the through-holes have a constant cross-section throughout the thickness;
    wherein at least one of said additional spacers comprises a first through-hole extending over about one half of the spacer's surface, and a plurality of second through-holes distributed on the other half of the spacer's surface.

13. A kit of parts for assembling a diffusive dosimeter for the detection of pollutants, said kit of parts comprising:
    a housing;
    a first adsorbent to be removably placed inside said housing;
    a first spacer to be removably placed on top of said adsorbent, to define a thickness and a first surface area of a diffusive layer,
    a first protective layer to be removably placed on top of said spacer;
    a first cover having an opening, to be removably placed on top of said protective layer, to close off the assembled dosimeter at the dosimeter's circumference;
    at least one additional spacer, each additional spacer being configured to replace said first spacer and defining the same thickness as the first spacer, wherein the first spacer and each additional spacer comprises one or more through-holes, the through-holes being different between the spacers so that each spacer defines a different surface area of the diffusive layer and provides for making a measurement with a different uptake rate, wherein the through-holes have a constant cross-section throughout the thickness;
    one additional cover, being a closed cover configured for replacement of the first cover.

14. A kit of parts for assembling a diffusive dosimeter for the detection of pollutants, said kit of parts comprising:
    a housing,
    a first adsorbent to be removably placed inside said housing,
    a first spacer to be removably placed on top of said adsorbent, to define a thickness and a first surface area of a diffusive layer,
    a first protective layer to be removably placed on top of said spacer, a first cover having an opening, to be removably placed on top of said protective layer, to close off the assembled dosimeter at the dosimeter's circumference, at least one additional spacer, each additional spacer being configured to replace said first spacer and defining the same thickness as the first spacer, wherein the first spacer and each additional spacer comprises one or more through-holes, the through-holes being different between the spacers so that each spacer defines a different surface area of the diffusive layer and provides for making a measurement with a different uptake rate, wherein the through-holes have a constant cross-section throughout the thickness;

wherein said housing is adapted to receive a cover on both sides of said housing and make a pollutant uptake measurement at both sides.

* * * * *